United States Patent [19]

Moore

[11] Plant 5,033

[45] Apr. 12, 1983

[54] ROSE PLANT

[76] Inventor: Ralph S. Moore, 2519 E. Noble Ave., Visalia, Calif. 93277

[21] Appl. No.: 308,799

[22] Filed: Oct. 5, 1981

[51] Int. Cl.[3] ..... A01H 5/00

[52] U.S. Cl. ..... Plt./9

[58] Field of Search ..... Plt./9

*Primary Examiner*—Robert E. Bagwill

[57] ABSTRACT

This invention relates to a new and distinct variety of miniature rose plant primarily identified by its vigorous growth habit and the abundance of rose pink buds and flowers.

1 Drawing Figure

The present invention relates to a new and distinct variety of hardy, dwarf, bush type rose plant of the miniature class; the variety being primarily characterized—as to novelty—by the rose pink buds and flowers which generally are of exhibition (Hybrid Tea) form.

The variety is further characterized by:

An abundance of bloom, with flowers usually borne singly, but also several to the stem in loose clusters.

Little or no fragrance.

A plant which is vigorous, of rounded, upright shape with small semi-glossy to matte foliage with pointed leaflets; the buds and flowers being similar in form to Mary Marshall (miniature—U.S. Plant Pat. No. 3,346) but of somewhat larger size.

The plant, which has a normal height of 14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Baccara (U.S. Plant Pat. No. 1,367—expired) as the seed parent and Little Chief (miniature—not patented) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety identification.*—MORcara (Commercial synonym: Antique Rose).

Flowers borne: Singly and several together (3 to 5) on slender wirey stems.

Quantity of bloom: Abundant both outside and in greenhouse.

Bud:

*Peduncle.*—Medium length; slender but sturdy; erect; medium to light green, sometimes tinted bronze (outdoors); with no prickles and no hairs.

*Before calyx breaks.*—Size small. Form long; pointed with several foliaceous appendages and few or no hairs on surface of bud; with foliaceous parts extending beyond the tip of the bud equal to one-half or less of its length.

*Color.*—Medium green, occasionally tinted with bronze (outdoors).

*As calyx breaks.*—Color — pink to red.

*Opening.*—Opens well in all weather.

Bloom:

*Size when fully open.*—Small, averaging about 40–45 mm (1½–1¾").

*Petalage.*—Double — averaging about 35–45 petals, arranged regularly plus several small petaloids.

*Form.*—High centered at first becoming more open at maturity with petals rolled loosely outward and downward. Open flowers may show stamens.

Petals: Fairly thick; satiny on inside and on outside surface.

*Shape.*—Outside petals, broad lanceolate (nearly round); intermediate — broad lanceolate with short acute tip; inside — lanceolate to broad lanceolate with acute tip.

Color: Newly opened flower from a plant grown outdoors (September 1981), Visalia, Calif.

*Outside petal.*—Outside surface — near Rose Bengal 25/2 with small light greenish area at base. Inside surface — near Rose Bengal 25/2 (sometimes lighter) with small whitish to yellowish area at base.

*Intermediate petal.*—Outside surface — near Rose Bengal 25/1 with small light area at base. Inside surface — near Rose Bengal 25/2 with darker border (petal edges) similar to color of reverse side.

*Inner petal.*—Outsie surface — same as intermediate petal. Inside surface — same as intermediate petal.

*General color effect.*—Buds and newly opened flowers — rose pink; with outside surfaces appearing darker color then inside surfaces.

*Three days open.*—Color: similar to freshly opened flower.

*Behavior.*—Opens well in all weather. Spent petals drop off.

*Flower longevity (July-August* 1981).—Plant in pot 6-8 days or longer. Cut flowers at living room temperature 3-5 days or longer.

Reproductive organs:

*Stamens.*—Arranged regularly about pistils.

*Filaments.*—Varying length, medium long, reddish.

*Anthers.*—Well formed; yellow.

*Pollen.*—Little or none.

*Pistils.*—Average number.

*Styles.*—Varying length; reddish; bunched.

*Ovaries.*—All enclosed in calyx.

*Stigmas.*—Pinkish.

*Hips.*—None.

*Sepals.*—Permanent; spear shaped; recurved.

*Seed.*—None.

Foliage:

*Leaves.*—Compound of five (sometimes three or seven) leaflets; medium small; leathery; semi-glossy to matte.

*Leaflets.*—Shape: broad, lanceolate; apex acute; base acute, sometimes rounded. Color: medium green; new growth — normal (medium) green. Rachis: Medium strength; upper side may have several tiny short prickles or hairs; grooved; underside usually without thorns or hairs.

*Stipules.*—Long to medium length; medium width; medium length narrow points which turn out usually at about 45 degrees or more.

Growth:

*Habit.*—Dwarf; bushy; rounded; much branched.

*Growth.*—Free vigorous; internodes short.

*Canes.*—Medium; slender; sturdy.

*Main stems.*—Color: medium green.

*Thorns.*—Moderately thorny — long oval base, points hooked (curved) downward; color — brown.

*Branches.*—Color: medium green.

*Thorns.*—Moderately thorny, slender, greenish.

*Prickles.*—None.

*Hairs.*—None.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit, substantially as illustrated and described, characterized by buds and flowers of exhibition form, essentially pink to rose pink in color and resembling Mary Marshall (miniature—U.S. Plant Pat. No. 3,346) in bud and flower form but being somewhat larger in size; and further characterized by a plant of compact well rounded shape with above average vigor, the said plant being easy to propagate from cuttings or by budding, with an abundance of small semi-glossy to matte foliage and an abundance of flowers borne singly or several to the stem in loose clusters.

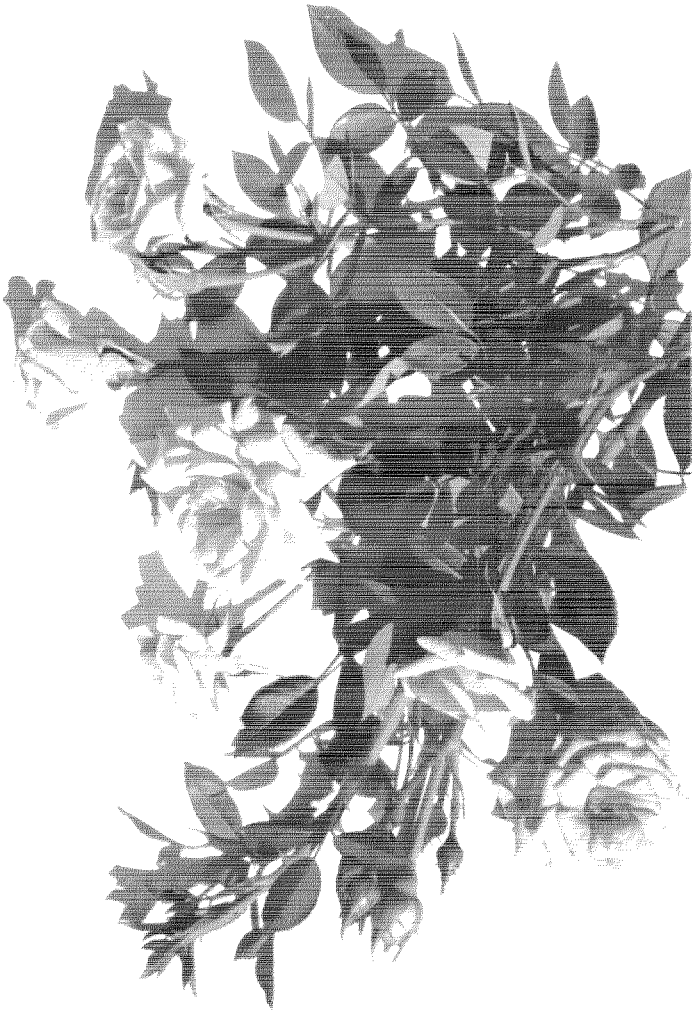

* * * * *